United States Patent
Filippova et al.

(10) Patent No.: US 8,613,961 B1
(45) Date of Patent: Dec. 24, 2013

(54) DERMATOLOGICAL CREAM WITH NATURAL INGREDIENTS BASE

(71) Applicant: NU Technology, LLC, Union Dale, PA (US)

(72) Inventors: Irina V Filippova, Union Dale, PA (US); Leonid K. Filippov, Union Dale, PA (US)

(73) Assignee: NU Technology, LLC, Union Dale, PA (US)

( * ) Notice: Subject to any disclaimer, the term of this patent is extended or adjusted under 35 U.S.C. 154(b) by 0 days.

(21) Appl. No.: 13/737,114

(22) Filed: Jan. 9, 2013

(51) Int. Cl.
*A61K 36/00* (2006.01)
*A61K 36/16* (2006.01)
*A61K 36/71* (2006.01)
*A61K 36/258* (2006.01)
*A61K 36/752* (2006.01)
*A01N 65/00* (2009.01)
*A01N 65/20* (2009.01)
*A01N 65/22* (2009.01)
*A61K 8/02* (2006.01)
*A61K 9/14* (2006.01)

(52) U.S. Cl.
USPC ........... 424/725; 424/726; 424/728; 424/736; 424/752; 424/775; 424/401; 424/489

(58) Field of Classification Search
USPC ......... 424/400, 401, 489, 725, 736, 726, 752, 424/728, 775
See application file for complete search history.

(56) References Cited

U.S. PATENT DOCUMENTS

| | | |
|---|---|---|
| 4,364,940 A | 12/1982 | Neiss et al. |
| 4,543,351 A | 9/1985 | Messina |
| 4,767,750 A | 8/1988 | Jacquet et al. |
| 5,344,850 A | 9/1994 | Hata et al. |
| 5,470,884 A | 11/1995 | Corless et al. |
| 5,476,852 A | 12/1995 | Cauwenbergh |
| 5,654,013 A | 8/1997 | Taylor et al. |
| 5,667,790 A | 9/1997 | Sellers, Jr. |
| 5,696,099 A | 12/1997 | della Valle et al. |
| 5,698,593 A | 12/1997 | Peck |
| 5,837,270 A | 11/1998 | Burgess |
| 5,952,372 A | 9/1999 | McDaniel |
| 5,972,993 A | 10/1999 | Ptchelintsev |
| 5,976,565 A | 11/1999 | Fotinos |
| 5,994,330 A | 11/1999 | El Khoury |
| 7,364,732 B2 | 4/2008 | Thompson et al. |
| 8,192,749 B2 | 6/2012 | Ashley |
| 8,268,367 B2 | 9/2012 | Chaudhary |
| 8,268,790 B2 | 9/2012 | McDonagh et al. |
| 8,313,782 B2 | 11/2012 | Guthery |
| 2004/0234628 A1* | 11/2004 | Kearns et al. .................. 424/736 |
| 2005/0032900 A1* | 2/2005 | Krauser ......................... 514/570 |
| 2005/0255076 A1 | 11/2005 | Santo et al. |
| 2007/0154402 A1* | 7/2007 | Trumbore et al. .............. 424/45 |
| 2008/0317795 A1* | 12/2008 | Traynor et al. ................ 424/401 |
| 2010/0215634 A1 | 8/2010 | Tennenbaum et al. |
| 2011/0159077 A1 | 6/2011 | Figueroa Lizama |
| 2011/0207696 A1 | 8/2011 | Mailland et al. |

FOREIGN PATENT DOCUMENTS

| | | | | |
|---|---|---|---|---|
| WO | 2005097084 | | 10/2005 | |
| WO | WO2006096955 | * | 9/2006 | ............. A61K 47/08 |

OTHER PUBLICATIONS

Stewart, J.C. M., et al. "Treatment of Severe and Moderately Severe Atopic Dermatitis with Evening Primrose Oil (Epogam): A Multi-centre Study", ResearchGate, Jul. 2009. Abstract only.

Saeedi, M., "The treatment of atopic dermatitis with licorice gel", J. Dermatolog. Treat., Sep. 14, 2003, Abstract only.

* cited by examiner

*Primary Examiner* — Rachael E Bredefeld

(74) *Attorney, Agent, or Firm* — Joseph E. Maenner; Maenner & Associates, LLC

(57) ABSTRACT

A dermatological cream includes between about 8% and about 25% by weight of a healing oil; between about 3% and about 8% by weight of an herbal extract; between about 0.1% and about 0.6% by weight of vitamin E; a microencapsulated ingredient selected from the group consisting of: about 0.6% by weight capsaicin, between about 2% and about 2.5% by weight capsiscum, about 6% by weight methylsulfonyl-methane, about 2% by weight collagen peptides, about 5% by weight azealic acid, between about 2% and about 15% by weight ibuprofen, between about 4% and about 10% by weight sulfur, between about 2% and about 15% by weight zinc oxide, between about 5% and about 8% by weight vitamin C, between about 0.5% and about 1% by weight vitamin A, between about 4% and about 8% by weight menthol, between about 3% and about 6% by weight camphor, about 0.5% by weight nicotinic acid, between about 3% and about 5% by weight amino acids, and between about 3% and about 6% by weight tea tree oil; and at least 43.4% by weight water.

18 Claims, No Drawings

DERMATOLOGICAL CREAM WITH NATURAL INGREDIENTS BASE

FIELD OF THE INVENTION

The present invention relates to the dermatological cream compositions for topical treatment of acne, rosacea, bruises, fungus, yeasts infection, arthritis, pain, bedsores & pressure sores, shingles, psoriasis, eczema, atopic dermatitis (as a common type of dermatitis), and skin disorders such as bruises, swollen, skin pain, itching, redness, inflammation and the frequency of skin flare ups. The present invention is also concerned with the topical treatment of acneiform dermal disorders such as preadolescent acne, acne rosacea, premenstrual acne, acne venenata, acne cosmetic, steroid acne, and acne conglobata. The present invention may also be used for topical treatment of another acneiform dermal disorders such as gram negative folliculitis, periodical and seborrheic dermatitis, folliculitis, and sebaceous gland dysfunction.

The present invention relates to topical compositions of: (a) mixture of plant oils having biologically active ingredients, (b) water-soluble ibuprofen (and/or other NSAIDs), (c) water-soluble microencapsulated sulfur and zinc oxide, (d) active natural botanic extracts, (e) amino acids, and (f) water-soluble microencapsulated vitamins C and A.

BACKGROUND OF THE INVENTION

Numerous dermatological products are available to treat different skin afflictions. These products, however either do not fully treat the particular skin afflictions for which they are being used or generate severe side effects.

There exists a need to provide products that are able to treat acne, rosacea, fungus, yeasts infection, arthritis, pain, bedsores & pressure sores, shingles, psoriasis, eczema, atopic dermatitis (as a common type of dermatitis), and skin disorders over a short period of time without causing side effects.

BRIEF SUMMARY OF THE INVENTION

Briefly, the present invention provides a dermatological cream comprising between about 8% and about 25% by weight of a healing oil; between about 3% and about 8% by weight of an herbal extract; between about 0.1% and about 0.6% by weight of vitamin E; a microencapsulated ingredient selected from the group consisting of: about 0.6% by weight capsaicin, between about 2% and about 2.5% by weight capsiscum, about 6% by weight methylsulfonylmethane, about 2% by weight collagen peptides, about 5% by weight azealic acid, between about 2% and about 15% by weight ibuprofen, between about 4% and about 10% by weight sulfur, between about 2% and about 15% by weight zinc oxide, between about 5% and about 8% by weight vitamin C, between about 0.5% and about 1% by weight vitamin A, between about 4% and about 8% by weight menthol, between about 3% and about 6% by weight camphor, about 0.5% by weight nicotinic acid, between about 3% and about 5% by weight amino acids, and between about 3% and about 6% by weight tea tree oil; and at least 43.4% by weight water.

DETAILED DESCRIPTION OF THE INVENTION

Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

The inventors have formulated water-soluble compositions of dermatological creams using a natural ingredients base that are capable to treat successfully dermatological issues such as acne, rosacea, bruises, fungus, yeasts infection, arthritis, pain, bedsores & pressure sores, shingles, psoriasis, eczema, atopic dermatitis (as a common type of dermatitis), and skin disorders (such as bruise, swelling, skin pain, itching, redness, inflammation and the frequency of skin flare ups, and etc.) with low (in the most cases, no) skin irritation, itching, and skim discomfort and with low (in the most cases, without) side effects in particular for patients with sensitive and/or hypersensitive skin.

The present invention relates to therapeutic compositions for topical use in the treatment of acne, rosacea, bruises, fungus, yeasts infection, arthritis, pain, bedsores & pressure sores, shingles, psoriasis, eczema, atopic dermatitis (as a common type of dermatitis), and skin disorders, containing (1) water-soluble ibuprofen (and/or NSAIDs, (2) azealic acid, (3) water-soluble microencapsulated sulfur, zinc oxide, vitamin C (ascorbic acid), vitamin A (retinol A), (4) biologically active herbal extract (ingredients) such as goldenseal extract, bilberry extract, calendula officinalis flower extract, carrot seed extract, citrus seed extract, licorice extract, ginkgo biloba extract grapefruit seed extract, red clover, olive leaves extract, Siberian ginseng extract, St. John's wort extract, yarrow extract, willow bark extract, (5) natural healing oils such as blackcurrants seed oil, borage seed oil, primrose oil, dog rose hip oil, wild oregon oil, tamanu oil, sesame oil, cinnamon oil, chamomile oil, grape seed oil, lavender oil, clove oil, kiwi seed oil, tea tree oil, safflower oil, thymus oil, (6) salycic acid and vitamin E (dα Tocopherol) as natural anti-oxidant. Such compositions (having a sebum regulating activity associated with antiinflammatory and antibactetic effects) accelerate the healing of acne, rosacea, and dermatitis utilizing small amounts of the above-mentioned active ingredients, and, at the same time, maintaining moisture and elasticity of the skin. Due to the synergetic effect of the above-mentioned active ingredients, the treatment of the acne, rosacea, fungus, yeasts infection, arthritis, pain, bedsores & pressure sores, shingles, psoriasis, eczema, atopic dermatitis (as a common type of dermatitis), and skin disorders occurs much faster compared to the already known and currently used formulations. Topical administration of the small quantities of the above-mentioned dermatological cream may show an antikertinising effect on normal skin, as well as on acne-affected, rosacea-affected, and dermatitis-affected skin, an effect due to the decreased synthesis of filaggrin, keratin filament aggregating protein, inducing thus a reduction of follicular hyperkeratosis.

The inventors have formulated several compositions of dermatological creams using a natural ingredients base in the form of a water-soluble complex emulsion/suspension using a microencapsulation process using DownPore™ technology that enhances through-the-skin penetration of biological active ingredients through the normal, dry, and mature skin and as disclosed in U.S. Pat. No. 5,393,461 entitled "PREPARATION OF STABLE AQUEOUS EMULSION OF WATER-INSOLUBLE PARTICLES", which is incorporated herein by reference in its entirety. The inventive creams are in the form of stable water-soluble emulsions/suspensions in a temperature range between about 59° F. (about 15° C.) and about 95° F. (about 35° C.).

The DownPore™ microencapsulation process, which is also disclosed in U.S. Pat. No. 5,393,461, is a process that enhances through-the-skin penetration of biological active ingredients through the normal, dry, and mature skin. The complex emulsion/suspension (herein after referred to simply as an "emulsion") disclosed in U.S. Pat. No. 5,393,461 is an emulsion in which a dispersed phase contains another dispersed phase. The multiple emulsion is a water/oil/water (W/O/W) emulsion. A W/O/W emulsion is a system in which water globules are dispersed in oil globules, the latter being themselves dispersed in an aqueous phase. Multiple emulsions are sometimes called triple-phase emulsions. Multiple emulsion includes two immiscible liquids (water or oil); therefore, their preparation demands the presence of two emulsifiers (the primary and the secondary surfactants). A solid part of the product (or cream) consists of fine particles (with size of less than about 1 micron) of active ingredients.

The present invention relates to dermatological cream compositions to treat acne, rosacea, bruises, fungus, yeasts infection, arthritis, pain, bedsores & pressure sores, shingles, psoriasis, eczema, atopic dermatitis (as a common type of dermatitis), and skin disorder treatments over a short period of time without causing side effects. The inventors believe that the inventive cream compositions have high effectiveness, cause low (in the most cases, no) skin irritation, itching, or discomfort, cause small (in the most cases, no) side effects, and have good physical and chemical stability. These compositions comprise (a) a mixture of the plants' oils having biologically active ingredients, (b) the water-soluble microencapsulated ibuprofen (and/or NSAIDs), (c) the water-soluble microencapsulated sulphur, zinc oxide, and biological active natural ingredients, (d) biological active natural herbal extract (ingredients), and (e) the water-soluble microencapsulated vitamins C and A.

Several ingredients are common throughout most, if not all, of the dermatological creams of the present invention. The more commonly used ingredients are discussed in detail below.

Ibuprofen/NSAID

An active ingredient of the cream is microencapsulated water-soluble USP ibuprofen. Ibuprofen, in a class of drugs called nonsteroidal anti-inflammatory drug (NSAID), belonging to the group of propionic acid derivatives, inhibits the enzyme cyclo-oxygenase (prostaglandin synthesis), which catalyzes the transformation of unsaturated fatty acids to prostaglandins. It is believed that the inhibition of the prostaglandin synthesis is the cause for the analgesic, antipyreti, and anti-inflammatory action of the drug. Ibuprofen works by reducing hormones that cause inflammation and pain in the body. Ibuprofen is used to reduce the fever, pain, inflammation, and stiffness caused by many conditions.

The inventors recognize that long-term or extensive ingestion of NSAID can result in the drugs having toxicity to the kidneys and also to the lining of the stomach, possibly causing ulcers. Therefore, the inventors are using the Down-Pore™ technology disclosed in U.S. Pat. No. 5,393,461 to produce microencapsulated USP ibuprofen in the form of a stable water-soluble emulsion for dermatological treatment.

The inventive creams using water-soluble microencapsulated ibuprofen and/or other NSAIDs (between about 0% and about 15% by weight) include at least some of the following:

(i) Arylpropionic acids (e.g., ibuprofen, flurbiprofen, fenoprofen, naproxen, and oxaprozin), (ii) Salicylic acid derivatives (e.g., aspirin, salsalate, sodium salicylate, choline magnesium trisalicylate, sulfasalazine, olsalazine, and diflunisal), (iii) Anthranilic acids (e.g., mefenamic acid and meclofenamic acid), (iv) Heteroaryl acids (e.g., tolmetin, diclofenac, and ketorolac), (v) Enolic acids (e.g., piroxicam and meloxicam), (vi) Indole and Indene acetic acids (e.g., indomethacin and sulindac), (vii) Indole acetic acids (e.g., etodolac), (viii) Para-Aminophenol derivatives (e.g., acetaminophen or Tylenol®)

(ix) Alkanes (e.g., Nabumetone), (x) Diaryl-Substituted furanones (e.g., rofecoxib), (xi) Diaryl-Substituted pyrazoles (e.g., celecoxib), and (xii) Sulfonanilides (e.g., nimesulide).

Microencapsulated Water-Soluble USP Sulfur

Sulfur is a vital ingredient for many dermatological products. Sulfur is an excellent natural preservative since it has anti-inflammatory, anti-bacterial and anti-fungal properties. Exemplary medical uses of sulfur preparations are as fungicides and parasiticides, and for the treatment of various cutaneous disorders such as psoriasis, seborrhoea, eczema-dermatitis, and lupus erythermatosus. Sulfur kills bacteria on and in the skin. Sulfur converts to pentatonic acids in order to exert germicidal activity. Sulfur also possesses a keratolytic property, which is the basic property needed to treat certain cutaneous disorders unassociated with infection. Sulfur in the form of fine particles (with a size of less than 1 micron) is an anti-infective (fighting infection) agent and also reduces the activity of the sebaceous glands, thus dries the skin. Its principal remaining use is in the skin disorder treatment. The inventive creams include between about 0% and about 10% by weight of microencapsulated USP sulfur.

Microencapsulated Water-Soluble USP Zinc Oxide

Zinc oxide has been used in the treatment of literally hundreds of skin disorders and it has been at least partially successful in many of them. Zinc oxide has a mild astringent and antiseptic action. Zinc oxide is a Category I skin protector, and promotes healthy skin. Zinc oxide is used for treatment of skin diseases and infections such as eczema, impetigo, ringworm, varicose ulcers, pruritus, and psoriasis.

Zinc oxide regulates the activity of oil glands and is required for protein, DNA and RNA synthesis and collagen formation. Zinc oxide provides an excellent barrier to the sun and other irritants. Zinc oxide has been used in the treatment of literally hundreds of skin disorders and it has been at least partially successful in many of them. Additionally, zinc oxide is somewhat astringent, antiseptic, and anti-bactericidal.

The inventors have produced microencapsulated USP zinc oxide in the form of the stable water-soluble emulsion/suspension for dermatological application. The common active ingredient used in dermatological cream compositions is zinc oxide.

Zinc oxide in the form of fine particles (with a size of less than about 1 micron) is an astringent and antiseptic, with its principal remaining use in the skin disorder treatment. The inventive creams include between about 0% and about 15% by weight of microencapsulated USP zinc oxide.

Microencapsulated USP Vitamin C

Vitamin C (ascorbic acid) is reversibly oxidizable in the human body to a form known as dehydroascorbic acid. The physiological functions of vitamin C are related to this oxidation-reduction system. Vitamin C is involved in carbohydrate metabolism, reduction of glucose tolerance, and decrease of hepatic glycogen content and resistance to insulin. Vitamin C prevents the oxidation of epinephrine. A very important role of vitamin C is to decrease the rate of skin aging process and to increase the wound-healing process.

Unique properties of vitamin C are that it: (i) stimulates: (1) blood circulation, (2) cell regeneration, (3) skin immune system, (4) fibroblasts and keratinocytes to produce collagen, and (5) dermal penetration of the active ingredients through the skin, (ii) is an anti-inflammatory agent, (iii) increases skin metabolism, (iv) activates dermal enzymes, and (v) promotes faster healing due to quicker absorption and prolonged duration. Vitamin C is an antioxidant that is required for at least 300 metabolic functions in the body, including tissue growth and repair, adrenal gland function, and healthy gums.

However, vitamin C is unstable and quickly oxidizes with time. In order to decrease the rate of oxidation and increase the biological activity of vitamin C, the inventors have produced microencapsulated USP Vitamin C in the form of a stable water-soluble emulsion for dermatological application. The inventive creams include between about 0% and about 8% by weight of microencapsulated vitamin C.

Microencapsulated Water-Soluble Vitamin A

Vitamin A (Retinol A) has a number of important functions in the body. Vitamin A is essential for the integrity of epithelial cells and has a stabilizing effect on various membranes. Vitamin A also regulates membrane permeability and stimulates the synthesis of nuclear RNA, suggesting a role in genetic transcription and cell differentiation. Vitamin A is converted to a metabolite that is a true vitamin. Vitamin A is used for local treatments of infections, burns, and wounds.

Vitamin A is an anti-oxidant, which is a compound that may protect against disease by neutralizing unstable oxygen molecules, called free radicals, within the body. Vitamin A is involved in night vision, growth, cell differentiation and reproduction. Vitamin A also maintains the health of the skin (prevents acne and dermatitis) and surface tissues especially those with mucous linings. These linings are the body first defense against infection, which is why vitamin A helps fight colds and infections.

However, vitamin A is also unstable and quickly oxidizes with time. In order to decrease the rate of its oxidations and increase the biological activity of vitamin A, and the inventors have developed microencapsulated USP Vitamin A in the form of the stable water-soluble emulsion for dermatological application. The inventive creams include between about 0% and about 2% by weight of vitamin A.

Natural Healing Oils

The base of the effective topical compositions of derma cream is a good transdermal delivery, which provides transdermal transfer of biologically active ingredients across the skin barrier. Healing Oil (HO) is comprised of a mixture of different plants' oils having healing effect due to the presence of biological active ingredients.

Some plants have oils, which have been proven by scientific investigations to contain fatty acids essential to human health, while others contain specially effective ingredients, like azulene in chamomile and gamma-linolenic acid in evening primrose and borage. Azulene in volatile oils of chamomile have healing and anti-inflammatory properties. The inventors have formulated such a combination of plants' oils which helps to restore natural active ingredients in the skin and aids in healing various skin problems.

The inventors believe that never before has such a combination been formulated to help restore natural elements of the skin. HO, the mixture of plants' oils containing optimal balance of linolenic (Omega 3 Essential Fat Acid (EFA)) and linoleic (Omega 6) acids, provides moisturizing, protecting, softening, and soothing properties. Oleic acid, the most prevalent fatty acid in HO, is well-known for its capability of transporting bioactive ingredients through the skin. This penetrating capability of HO is a significant addition to its other purported characteristics. For example, hemp seed oil has one of the highest contents of essential fatty acids (EFAs) (including gamma linolenic acid): 76%. These EFAs present the best ratio between Omega-6 and Omega-3 acids: 3 to 1. They constitute the phospholipids necessary to build the cell membranes and a 3 to 1 ratio required in the human body for proper cell growth. It is noted that EFA's deficiency leads to skin diseases such as atopic eczema, psoriasis, epidermal scaling, increased Transdermal Water Loss (TEWL).

Gamma linolenic acid is naturally synthesized from linoleic acid by delta desaturase and is a key precursor of prostaglandins, which play a key role as biological mediators. Gamma linolenic acid is an essential fatty acid, metabolized by the organism in prostaglandins via di-homo-gamma-linolenic acid and arachidonic acid, which is itself a constituent of cellular membranes. In effect, a lack of essential fatty acids results in a nutritional deficiency affecting all the metabolic processes which have been mentioned above and which may result in biochemical disorders or in organic lesions (for example, coagulation disorders, dermatological lesions, endocrinal complaints, myocardial lesions, and hepatic).

The penetrating capability of HO is a significant addition to its other purported characteristics such as: (i) anti-inflammatory activity, (ii) penetration enhancement for topical skin products, (iii) significant epidermal proliferate activity, (iv) significant reduction of recent keloid scarring, (v) non-comedogenic (non-pore-clogging), (vi) stimulation of skin immune system, and (vii) promotion of faster healing due to quicker absorption and prolonged duration.

Virgin oils are useful and contain several natural active ingredients. For example, virgin olive oil (rich in monounsaturated fatty acids, vitamin E, coenzyme Q, poliphenols) protects plasma and subcellular membranes against damage. Commercial (refined) olive oil loses a high level of antioxidant compounds (vitamin E, coenzyme Q, poliphenols) during the extraction procedure. These losses in unsaponifiable fraction lead to a decrease in total antioxidant capacity in these oils. Natural healing oils included in the inventive creams may include one or more of blackcurrants seed oil, borage seed oil, dog rose hip oil, hazel nut oil, tamanu oil, sesame oil, chamomile oil, grape seed oil, lavender oil, clove oil, kiwi seed oil, tea tree oil, safflower oil, thymus oil, primrose oil, wild oregon oil, and cinnamon oil. The inventive creams include between about 18% and about 25% by weight of healing oils.

Herbal Extracts

Additionally, biological active herbal extracts included in the creams may include one or more of birch leave and bark extract, black nightshade extract, burdock extract, goldenseal extract, bilberry extract, calendula officinalis flower extract, carrot seed extract, comfrey leaf extract, grapefruit seed extract, olive leaves extract, St. John's wort extract, willow bark extract, carrot seed extract, citrus seed extract, licorice extract, ginkgo biloba extract, red clover, Siberian ginseng extract, and yarrow extract. The inventive creams include between about 0% and about 8% by weight of herbal extracts.

Amino Acids

The inventive creams may also include essential and non-essential amino acids. Any of the known or as yet unknown amino acids may be used. A single amino acid may be used or, alternatively, any combination of amino acids may be used. The inventive creams may include between about 0% and about 5% by weight of microencapsulated amino acids.

Other Ingredients

The inventive creams also include combinations of at least two of microencapsulated menthol (between about 0% and about 8% by weight), microencapsulated camphor (between about 0% and about 6% by weight), fumaric acid (between about 0% and about 8% by weight), microencapsulated capsaicin (between about 0% and about 0.06% by weight), microencapsulated capsicum (between about 0% and about 2.5% by weight), microencapsulated methyl sulfonylmethane (between about 0% and about 6% by weight), microencapsulated azealic acid (between about 0% and about 5% by weight), microencapsulated nicotinic acid (between about 0% and about 0.5% by weight), microencapsulated amino acids (between about 0% and about 5% by weight), microencapsulated tea tree oil (between about 0% and about 6% by weight); vitamin B6, B12 (between about 0% and about 2% by weight), ginseng extract (between about 0% and about 3% by weight), decyl-glycoside (about 30% by weight), aloe barbadensis vera (about 2% by weight), salicylic acid (between about 0% and about 2% by weight), vitamin E (dα Tocopherol) (between about 0.2% and about 0.6% by weight), microencapsulated collagen peptides (between about 0% and about 2% by weight), and water (between about 40.2% and about 65.2% by weight).

Exemplary compositions of the inventive creams are provided below. While the exemplary compositions listed below give percentages of ingredients by weight, it is contemplated that the weight percent of each ingredient may vary as much as ±5% of the total weight of the composition.

| NATURAL FUNGUS CREAM COMPOSITION | |
| --- | --- |
| Ingredients | Weight Percent (%) |
| microencapsulated Sulfur | 10 |
| microencapsulated Zinc Oxide | 2 |
| microencapsulated Tea Tree Oil | 6 |
| microencapsulated Nicotinic Acid | 0.5 |
| Healing Oil | 19 |
| Herbal Extract | 6.0 |
| Salicylic Acid | 2 |
| vitamin E (dα Tocopherol) | 0.2 |
| Water | Add to 100% |

The inventors believe that the inventive fungus cream (i) provides broad spectrum treatment of fungus infections in particular fungus infections for fingernail and toenails which have proven to be resistant to treatment, (ii) stimulates broad spectrum of anti-fungal, anti-microbial, antiviral, and anti-inflammation characteristics and high effectiveness for fungal infections treatment, (iii) stimulates epidermal proliferate activity, and (iv) stimulates blood circulation and immune system promote faster healing due to quicker absorption and prolonged duration.

| NATURAL SHINGLES CREAM COMPOSITION | |
| --- | --- |
| Ingredients | Weight Percent (%) |
| microencapsulated Sulfur | 8.0 |
| microencapsulated Ibuprofen | 6.0 |
| microencapsulated Amino Acids | 4 |
| Siberian Ginseng Extract | 3.0 |
| Vitamin B6, B12 | 2.0 |
| Healing Oil | 24 |
| Herbal Extract | 6.0 |
| Salicylic Acid | 1 |
| vitamin E (dα Tocopherol) | 0.3 |
| Water | Add to 100% |

The inventors believe that the inventive shingles cream (i) reduces chronic pain, itching, inflammation, and discomfort during the shingles healing process, (ii) stimulates a broad spectrum of painkiller and neurotransmitters activities, (iii) stimulates epidermal proliferate activity, (iv) stimulates blood circulation and clean capillary, and (v) promotes faster healing due to quicker absorption and prolonged duration.

| ANTI-INFLAMMATION & PAIN KILLER IBUPROFEN CREAM COMPOSITION | |
| --- | --- |
| Ingredients | Weight Percent (%) |
| microencapsulated Ibuprofen | 15 |
| microencapsulated Amino Acids | 3 |
| Healing Oil | 25 |
| Herbal Extract | 6.0 |
| vitamin E (dα Tocopherol) | 0.2 |
| Water | Add to 100% |

The inventors believe that the inventive anti-inflammation and pain killer cream is effective to treat skin disorders including bruises, swelling, skin pain, itching, redness, inflammation and the frequency of skin flare ups. The inventive anti-inflammation and pain killer cream (1) provides moist, anti-bacterial, anti-microbial, anti-inflammation, pain relieving environment around affected skin surface, (2) creams affected skin surface by removal of dissolved pus, (3) stimulates antibacterial and antimicrobial activities, (4) decreases transdermal water loss, (5) reduces irritation, itching, and discomfort of the skin, (6) dissolves pus, and (7) stimulates blood circulation.

| YEAST INFECTION CREAM COMPOSITION | |
| --- | --- |
| Ingredients | Weight Percent (%) |
| microencapsulated Sulfur | 8.0 |
| microencapsulated Zinc Oxide | 2.0 |
| microencapsulated Ibuprofen | 2.0 |
| Tea Tree Oil | 3.0 |
| microencapsulated Amino Acids | 3 |
| Healing Oil | 24 |
| Herbal Extract | 6.0 |
| Salicylic Acid | 0.5 |
| vitamin E (dα Tocopherol) | 0.2 |
| Water | Add to 100% |

The inventors believe that the inventive yeast infection cream (i) prevents against new yeast infection disease from forming, (ii) provides a broad spectrum treatment of yeast infections, and in particular, yeast vaginal infections that have proven to be resistant to treatment, (iii) stimulates a broad spectrum of anti-yeast, anti-microbial, antiviral, and anti-inflammation characteristics and high effectiveness for yeast infections treatment, (iv) stimulates epidermal proliferate activity, (v) stimulates blood circulation and immune system, and (v) promotes faster healing due to quicker absorption and prolonged duration.

| PAIN KILLER CREAM (with Cooling Effects) COMPOSITION | |
| --- | --- |
| Ingredients | Weight Percent (%) |
| microencapsulated Camphor | 6 |
| microencapsulated Menthol | 8 |
| microencapsulated Ibuprofen | 3 |

-continued

PAIN KILLER CREAM
(with Cooling Effects) COMPOSITION

| Ingredients | Weight Percent (%) |
| --- | --- |
| Healing Oil | 22 |
| Herbal Extract | 5.0 |
| Salicylic Acid | 1 |
| vitamin E (dα Tocopherol) | 0.2 |
| Water | Add to 100% |

The inventors believe that the painkiller cream with cooling effects (1) provides temporary relief for the minor aches and pains of simple backache, bruises, sprains, muscles, joint pain associated with trauma, swollen, and arthritis, (2) stimulates broad spectrum of anti-inflammatory and painkiller activities, (3) stimulates fast-acting pain relief, (4) stimulates blood circulation and immune system, and (5) promotes faster healing due to quicker absorption and prolonged duration.

PAIN KILLER CREAM
(with Warming Effects) COMPOSITION

| Ingredients | Weight Percent (%) |
| --- | --- |
| microencapsulated Capsicum | 2.5 |
| (with Capsaicin) | 0.06 |
| microencapsulated Camphor | 3 |
| microencapsulated Ibuprofen | 3 |
| microencapsulated Amino Acids | 3 |
| Healing Oil | 25 |
| Herbal Extract | 6.0 |
| Salicylic Acid | 1 |
| vitamin E (dα Tocopherol) | 0.2 |
| Water | Add to 100% |

The inventors believe that the inventive painkiller cream with warming effects (1) provides temporary relief pains of simple backache, sprains, muscles, (2) stimulates broad spectrum of anti-inflammatory and painkiller activities, (3) stimulates fast-acting pain relief, (4) stimulates blood circulation and immune system, and (5) promotes faster healing due to quicker absorption and prolonged duration.

PSORIASIS CREAM COMPOSITION

| Ingredients | Weight Percent (%) |
| --- | --- |
| Fumaric Acid | 8 |
| microencapsulated Ibuprofen | 3 |
| microencapsulated Sulfur | 6 |
| microencapsulated Amino Acids | 5 |
| Healing Oil | 22 |
| Herbal Extract | 6 |
| Salicylic Acid | 0.5 |
| vitamin E (dα Tocopherol) | 0.3 |
| Water | Add to 100% |

The inventive psoriasis cream contains fumeric acid as active ingredient. Fumaric acid is the trans isomer of malic acid and an intermediate in the Krebs citric acid cycle. Psoriasis is regarded as a disease resulting from a metabolic error and, possibly, a defect of fumaric acid metabolism. Since the citric cycle is the center for energy production with the cell, fumaric acid must be present in every cell of the body; therefore, it is metabolically very active. The administration of the fumaric acid must be slow, as it is a metabolically very active.

The inventors believe that the inventive psoriasis cream (1) decreases transdermal water loss, (2) reduces irritation, itching, and discomfort of the skin, (3) stimulates antiviral, antibacterial, and anti-microbial activities, and epidermal proliferate activity of the skin, (4) promotes faster healing due to quicker absorption and prolonged duration, and (5) stimulates blood circulation.

NATURAL ECZEMA CREAM COMPOSITION

| Ingredients | Weight Percent (%) |
| --- | --- |
| Salicylic Acid | 1 |
| microencapsulated Sulfur | 6 |
| microencapsulated Vitamin C | 5 |
| microencapsulated Amino Acids | 4 |
| microencapsulated Vitamin A | 1.0 |
| Healing Oil | 25 |
| Herbal Extract | 8 |
| vitamin E (dα Tocopherol) | 0.6 |
| Water | Add to 100% |

The inventors believe that the inventive eczema cream (1) decreases transdermal water loss, (2) reduces irritation, itching, and discomfort of the skin, (3) stimulates antiviral, antibacterial, and anti-microbial activities, and epidermal proliferate activity of the skin, (4) promotes faster healing due to quicker absorption and prolonged duration, and (5) stimulates blood circulation.

DERMATITIS CREAM COMPOSITION

| Ingredients | Weight Percent (%) |
| --- | --- |
| microencapsulated Vitamin C | 8 |
| microencapsulated Ibuprofen | 5 |
| microencapsulated Sulfur | 9 |
| microencapsulated Amino Acids | 4.0 |
| microencapsulated Vitamin A | 0.5 |
| Healing Oil | 19 |
| Herbal Extract | 6 |
| Salicylic Acid | 1 |
| vitamin E (dα Tocopherol) | 0.2 |
| Water | Add to 100% |

The inventors believe that the inventive dermatitis cream (i) decreases transdermal water loss, (ii) reduces irritation, itching, and discomfort of the skin, (iii) stimulates antiviral, antibacterial, and anti-microbial activities, and epidermal proliferate activity of the skin, (iv) promotes faster healing due to quicker absorption and prolonged duration, and (v) stimulates blood circulation.

ZINC OXIDE CREAM COMPOSITION

| Ingredients | Weight Percent (%) |
| --- | --- |
| microencapsulated Zinc Oxide | 15.0 |
| microencapsulated Ibuprofen | 3.0 |
| microencapsulated Sulfur | 4.0 |
| microencapsulated Vitamin A | 0.5 |
| microencapsulated Amino Acids | 3 |
| Healing Oil | 24 |
| Herbal Extract | 6.0 |
| Salicylic Acid | 1 |
| vitamin E (dα Tocopherol) | 0.1 |
| Water | Add to 100% |

The inventors believe that the inventive zinc oxide cream is very effective for the treatment of skin disorders such as skin pain, itching, redness, inflammation and the frequency of skin flare ups. Zinc oxide (an essential mineral) regulates the activity of oil glands and is required for protein, DNA and RNA synthesis and collagen formation. Zinc oxide has a mild astringent and antiseptic action, and also is an effective preservative. Zinc oxide has been used in the treatment of literally hundreds of skin disorders and it has been partially successful in many of them. Zinc oxide for instant bleaching and sun protection protects, soothes and heals the skin. Zinc oxide is an excellent barrier to the sun and other irritants and is somewhat astringent, antiseptic, and anti-bactericidal. Zinc oxide cream increases the regeneration of skin affected by burns and wounds.

ARTHITIS CREAM COMPOSITION

| Ingredients | Weight Percent (%) |
| --- | --- |
| microencapsulated Capsicum | 2.0 |
| (with Capsaicin) | 0.06 |
| microencapsulated Sulfur | 4 |
| microencapsulated Ibuprofen | 4 |
| microencapsulated Collagen peptides | 2 |
| microencapsulated MSM (methylsulfonylmethane) | 6 |
| microencapsulated Amino Acids | 3 |
| Healing Oil | 20 |
| Herbal Extracts | 5 |
| Salicylic Acid | 1 |
| vitamin E (dα Tocopherol) | 0.1 |
| Water | Add to 100% |

The inventive arthritis cream contains microencapsulated sulphur and MSM. Sulfur is an essential component in the GAG (or glycosaminoglycans) compounds that constitute most cartilage tissue, and arthritis patients are often lacking in this overlooked element. The success of glucosamine sulfate may gain it more attention, since many believe that its beneficial effects are traceable to its sulfur content. Two other sulfur compounds—MSM (methylsulfonylmethane) and DMSO (dimethylsulfoxide)—have drawn attention as potential arthritis remedies. MSM is a natural sulfur "donor".

The inventors believe that the inventive arthritis cream composition (1) stimulates a broad spectrum of anti-inflammatory and painkiller activities, (2) stimulates fast-acting pain relief, (3) improves circulation and cleans capillaries, (4) decreases swelling, redness, and pain, (5) increases the skin metabolism and immune system, (6) stimulates blood circulation, smooth muscle activity, cell regeneration, and circulation of cardiovascular system, and (7) promotes faster healing due to quicker absorption and prolonged duration.

BEDSORE & PRESSURE SORE CREAM COMPOSITION

| Ingredients | Weight Percent (%) |
| --- | --- |
| microencapsulated Zinc Oxide | 2.5 |
| microencapsulated Ibuprofen | 4 |
| microencapsulated Sulfur | 6 |
| Camphor | 3.5 |
| Menthol | 4 |
| microencapsulated Amino Acids | 3 |
| Healing Oil | 23 |
| Herbal Extracts | 6.0 |
| Salicylic Acid | 0.5 |
| vitamin E (dα Tocopherol) | 0.3 |
| Water | Add to 100% |

The inventors believe that the inventive bedsores and pressure sores cream (1) decreases transdermal water loss, (2) prevents healthy tissue from the being compromised or destroyed by infection, (3) encourages new skin growth, (4) keeps the wound free infection, (5) helps leave the surface of wounds clean and odor free, (6) helps to maintain a bacteria-free environment, (7) reduces irritation, itching, and discomfort of the skin, (8) stimulates antiviral, antibacterial, and anti-microbial activities, and epidermal proliferate activity of the skin, (9) promotes faster healing due to quicker absorption and prolonged duration, and (10) stimulates of blood circulation.

ACNE CREAM COMPOSITION

| Ingredients | Weight Percent (%) |
| --- | --- |
| microencapsulated Ibuprofen | 1 |
| microencapsulated Sulfur | 9 |
| microencapsulated Zinc Oxide | 2 |
| Healing Oil | 18 |
| Herbal Extracts | 4.0 |
| Salicylic Acid | 0.5 |
| vitamin E (dα Tocopherol) | 0.3 |
| Water | Add to 100% |

The inventors believe that the inventive acne cream composition (1) reduces inflammation, (2) stimulates antibacterial and antimicrobial activities, (3) decreases transdermal water loss, (4) increases cellular turnover, (5) strengthens skin, (6) diminishes appearance of broken capillaries, (7) stimulates as a co-factor the production of collagen, (8) improves tone and texture, (9) reduces irritation, itching, and discomfort of the skin, and (10) stimulates blood circulation.

ROSACEA CREAM COMPOSITION

| Ingredients | Weight Percent (%) |
| --- | --- |
| microencapsulated Ibuprofen | 2 |
| microencapsulated azealic acid | 5 |
| microencapsulated Sulfur | 8 |
| microencapsulated Zinc Oxide | 1.5 |
| Healing Oil | 20 |
| Herbal Extracts | 6.0 |
| Salicylic Acid | 0.3 |
| vitamin E (dα Tocopherol) | 0.3 |
| Water | Add to 100% |

The inventors believed that the inventive rosacea cream composition (1) reduces facial swelling, burning, itching, inflammation, irritation, and discomfort of the skin, (2) removes visible blood vessels and reduce extensive redness, (3) stimulates antibacterial and antimicrobial activities, (4) decreases transdermal water loss, (5) stimulates of blood circulation, (6) controls excess oil, and (7) clears up pores.

| THERAPEUTICAL SHAMPOO FOR SEBORRHEA & DANDRUFF COMPOSITION ||
| --- | --- |
| Ingredients | Weight Percent (%) |
| Decyl-Glycoside | 30 |
| microencapsulated sulfur | 9 |
| microencapsulated Vitamin C | 5 |
| microencapsulated Ibuprofen | 2 |
| Aloe Barbadensis Vera | 2 |
| Healing Oil | 8 |
| Herbal Extracts | 3 |
| Salicylic Acid | 0.5 |
| vitamin E (dα Tocopherol) | 0.3 |
| Water | Add to 100% |

The inventors believe that the inventive therapeutic shampoo for seborrhea & dandruff composition is an effective treatment seborrhea & dandruff of scalp due to water-soluble microencapsulated sulfur, Vitamin C, and ibuprofen. The therapeutic shampoo is also believed to be effective against redness, itching, inflammation, irritation, and discomfort of the skin.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A dermatological cream comprising:
   between about 8% and about 25% by weight of a healing oil, the healing oil comprising blackcurrants seed oil, borage seed oil, dog rose hip oil, tamanu oil, sesame oil, chamomile oil, grape seed oil, lavender oil, and safflower oil;
   between about 3% and about 8% by weight of an herbal extract;
   between about 0.1% and about 0.6% by weight of vitamin E;
   a microencapsulated ingredient comprising up to about 15% by weight ibuprofen;
   a microencapsulated ingredient comprising up to about 10% by weight sulfur;
   a microencapsulated ingredient comprising up to about 15% by weight zinc oxide; and
   at least 40.2% by weight water.

2. The dermatological cream according to claim 1, further comprising between about 0.3% and about 2% by weight of salicylic acid.

3. The dermatological cream according claim 1, further comprising about 8% by weight of fumaric acid.

4. The dermatological cream according to claim 1, further comprising up to about 3% by weight of ginseng extract.

5. The dermatological cream according to claim 1, further comprising about 30% by weight of decyl-glycoside and about 2% by weight of aloe barbadensis vera.

6. The dermatological cream according to claim 1, further comprising a microencapsulated ingredient comprising up to about 1% vitamin A.

7. The dermatological cream according to claim 1, further comprising a microencapsulated ingredient comprising up to about 8% by weight vitamin C.

8. The dermatological cream according to claim 1, further comprising a microencapsulated ingredient comprising up to about 2.5% by weight capsicum.

9. The dermatological cream according to claim 1, further comprising a microencapsulated ingredient comprising up to about 5% by weight azealic acid.

10. The dermatological cream according to claim 1, further comprising a microencapsulated ingredient comprising up to about 6% by weight tea tree oil.

11. The dermatological cream according to claim 1, further comprising a microencapsulated ingredient comprising up to about 6% by weight methylsulfonylmethane.

12. The dermatological cream according to claim 1, further comprising a microencapsulated ingredient comprising up to about 3% by weight amino acids.

13. The dermatological cream according to claim 1, further comprising up to about 6% by weight camphor.

14. A dermatological cream comprising:
   between about 8% and about 25% by weight of a healing oil,
   between about 3% and about 8% by weight of an herbal extract, wherein the herbal extract comprises goldenseal extract, calendula officinalis flower extract, grapefruit seed extract, willow bark extract, citrus seed extract, ginkgo biloba extract, red clover, and Siberian ginseng extract;
   between about 0.1% and about 0.6% by weight of vitamin E;
   a microencapsulated ingredient comprising up to about 15% by weight ibuprofen;
   a microencapsulated ingredient comprising up to about 10% by weight sulfur;
   and at least 40.2% by weight water.

15. The dermatological cream according claim 14, wherein the healing oil is blackcurrants seed oil, borage seed oil, dog rose hip oil, tamanu oil, sesame oil, chamomile oil, grape seed oil, lavender oil, and safflower oil.

16. A dermatological cream for providing through-skin penetration, the cream in the form of an water/oil/water emulsion comprising:
   between about 8% and about 25% by weight of a healing oil, the healing oil comprising blackcurrants seed oil, borage seed oil, dog rose hip oil, tamanu oil, sesame oil, chamomile oil, grape seed oil, lavender oil, and safflower oil; between about 3% and about 8% by weight of an herbal extract; between about 0.1% and about 0.6% by weight of vitamin E;
   a microencapsulated ingredient comprising up to about 15% by weight ibuprofen;
   a microencapsulated ingredient comprising up to about 10% by weight sulfur;
   a microencapsulated ingredient comprising up to about 15% by weight zinc oxide; and
   at least 40.2% by weight water.

17. The dermatological cream according to claim 16, wherein each of the microencapsulated ingredients has a particle size of of less than about 1 micron.

18. The dermatological cream according to claim 16, wherein the cream is used to treat acne, rosacea, bruises, fungus, yeast infection, arthritis, pain, bedsores and pressure sores, shingles, psoriasis, eczema, atopic dermatitis, and skin disorders.

* * * * *